United States Patent
Tamura

(10) Patent No.: US 7,867,733 B2
(45) Date of Patent: Jan. 11, 2011

(54) METHOD FOR PRODUCING FACTOR G DERIVED FROM HORSESHOE CRAB

(75) Inventor: Hiroshi Tamura, Tokyo (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 12/430,681

(22) Filed: Apr. 27, 2009

(65) Prior Publication Data

US 2010/0112668 A1 May 6, 2010

Related U.S. Application Data

(62) Division of application No. 11/387,443, filed on Mar. 23, 2006, now Pat. No. 7,541,162.

(60) Provisional application No. 60/665,779, filed on Mar. 28, 2005.

(51) Int. Cl.
*C12P 21/06* (2006.01)
*C12N 5/10* (2006.01)

(52) U.S. Cl. .................................. 435/69.1; 435/348

(58) Field of Classification Search ................ 435/183
See application file for complete search history.

(56) References Cited

U.S. PATENT DOCUMENTS

| 5,795,962 A | 8/1998 | Iwanaga et al. |
|---|---|---|
| 6,077,946 A | 6/2000 | Iwanaga et al. |

OTHER PUBLICATIONS

BD Biosciences, "BD BaculoGold pVL1392 Product Details", "www.bdbiosciences.com/ptProduct.jsp? prodId=19996", Jul. 18, 2007.
Bowie et al., "Deciphering the Message in Protein Sequences: Tolerance to Amino Acid Substitutions", "Science", 1990, pp. 1306-1310, vol. 247.
Licari, et al., "Factors Influencing Recombinant Protein Yields in an Insect Cell . . . ", "Biotechnology and Bioengineering", 1991, pp. 238-246, vol. 37, Publisher: John Wiley & Sons, Inc.
Muta et al., "Purified Horseshoe Crab Factor G", "The Journal of Biological Chemistry", Jan. 13, 1995, pp. 892-897, vol. 270, No. 2, Publisher: The American Society for Biochemistry and Molecular Biology, Inc.
Possee, "Baculoviruses as expression vectors", "Current Opinion in Biotechnology", 1997, pp. 569-572, vol. 8, No. 5, Publisher: XP002384177 ISSN: 0958-1669, Published in: US.
WWW.THEFREEDICTIONARY.COM/REPRESENTED, "Definition of the term 'represented'", Apr. 15, 2008.
Seki et al., "Horseshoe Crab (1,3) . . . ", "The Journal of Biological Chemistry", Jan. 14, 1994, pp. 1370-1374, vol. 269, No. 2, Publisher: The American Society for Biochemistry and Molecular Biology, Inc.
Takaki et al., "Duplicated Binding Sites . . . ", "The Journal of Biological Chemistry", Apr. 19, 2002, pp. 14281-14287, vol. 277, No. 16, Publisher: The American Society for Biochemistry and Molecular Biology, Inc.
Wells, "Additivity of Mutational Effects in Proteins", "Biochemistry", Sep. 18, 1990, pp. 8509-8517, vol. 29, No. 37, Publisher: The Amercian Chemical Society.

*Primary Examiner*—Suzanne M. Noakes
(74) *Attorney, Agent, or Firm*—Factor & Lake, Ltd.

(57) ABSTRACT

The invention provides a virus harboring a DNA encoding a subunit of *limulus*-derived factor G, the virus being capable of mass-producing a $(1 \rightarrow 3)$-$\beta$-D-glucan assay reagent of satisfactory quality, steadily and at low cost, a cell harboring the virus, and a method of producing factor G by use of the cell.

7 Claims, No Drawings

SEQUENCE LISTING

<160> NUMBER OF SEQ ID NOS: 19

<210> SEQ ID NO 1
<211> LENGTH: 2059
<212> TYPE: DNA
<213> ORGANISM: Tachypleus tridentatus
<220> FEATURE:
<221> NAME/KEY: CDS
<222> LOCATION: (1)..(2058)

<400> SEQUENCE: 1

```
atg ttg gtg ttg ctg tgt tgt gtt gtt ttg cat gtt ggt gtt gca aga      48
Met Leu Val Leu Leu Cys Cys Val Val Leu His Val Gly Val Ala Arg
1               5                   10                  15 att tgc tgt agc cac gaa cca aag tgg cag ctc gtc tgg tcg gat gaa      96
Ile Cys Cys Ser His Glu Pro Lys Trp Gln Leu Val Trp Ser Asp Glu
                20                  25                  30 ttt acc aat gga ata agt tct gat tgg gaa ttt gaa atg ggc aat ggc     144
Phe Thr Asn Gly Ile Ser Ser Asp Trp Glu Phe Glu Met Gly Asn Gly
            35                  40                  45 ctc aat ggt tgg ggt aat aac gaa ctg caa tat tat cgt cgt gaa aat     192
Leu Asn Gly Trp Gly Asn Asn Glu Leu Gln Tyr Tyr Arg Arg Glu Asn
        50                  55                  60 gcc caa gtt gag gga ggg aaa ctg gta att act gct aaa aga gaa gac     240
Ala Gln Val Glu Gly Gly Lys Leu Val Ile Thr Ala Lys Arg Glu Asp
65                  70                  75                  80 tat gat ggc ttc aaa tac act tct gct agg ctg aaa acc cag ttt gat     288
Tyr Asp Gly Phe Lys Tyr Thr Ser Ala Arg Leu Lys Thr Gln Phe Asp
                85                  90                  95 aaa tct tgg aag tat ggt aaa att gaa gcc aaa atg gcg att cca tca     336
Lys Ser Trp Lys Tyr Gly Lys Ile Glu Ala Lys Met Ala Ile Pro Ser
            100                 105                 110 ttt cgg gga gtc tgg gtg atg ttc tgg atg tca gga gac aac act aat     384
Phe Arg Gly Val Trp Val Met Phe Trp Met Ser Gly Asp Asn Thr Asn
        115                 120                 125 tat gtt aga tgg cca tct tct ggt gaa att gac ttt att gaa cat aga     432
Tyr Val Arg Trp Pro Ser Ser Gly Glu Ile Asp Phe Ile Glu His Arg
    130                 135                 140 aac act aac aat gaa aaa gtc aga gga act att cac tgg tcc act cct     480
Asn Thr Asn Asn Glu Lys Val Arg Gly Thr Ile His Trp Ser Thr Pro
145                 150                 155                 160 gac ggt gct cat gcg cat cat aac aga gaa agt aat aca aat ggg att     528
Asp Gly Ala His Ala His His Asn Arg Glu Ser Asn Thr Asn Gly Ile
                165                 170                 175 gat tat cac att tat tct gta gag tgg aat tct tcc att gtt aaa tgg     576
Asp Tyr His Ile Tyr Ser Val Glu Trp Asn Ser Ser Ile Val Lys Trp
            180                 185                 190 ttt gtt aat gga aat caa tac ttt gaa gtg aaa att cag gga gga gta     624
Phe Val Asn Gly Asn Gln Tyr Phe Glu Val Lys Ile Gln Gly Gly Val
        195                 200                 205 aat ggg aaa agt gca ttt cgt aac aaa gtt ttc gtt att tta aac atg     672
Asn Gly Lys Ser Ala Phe Arg Asn Lys Val Phe Val Ile Leu Asn Met
    210                 215                 220 gcg att ggt gga aac tgg cca gga ttc gat gtt gct gac gag gct ttc     720
Ala Ile Gly Gly Asn Trp Pro Gly Phe Asp Val Ala Asp Glu Ala Phe
225                 230                 235                 240 cct gct aaa atg tac att gat tat gtc cgt gta tac cag gat gcc agt     768
Pro Ala Lys Met Tyr Ile Asp Tyr Val Arg Val Tyr Gln Asp Ala Ser
                245                 250                 255
```

-continued

| | | |
|---|---|---|
| aca tct tct cct gtt ggg gat acc tct tta gat ggt tac tat ttt gtc<br>Thr Ser Ser Pro Val Gly Asp Thr Ser Leu Asp Gly Tyr Tyr Phe Val<br>260 265 270 | | 816 |
| caa aac agg cac agt gaa ttg tat ctt gat gtc act gat gcc agt aac<br>Gln Asn Arg His Ser Glu Leu Tyr Leu Asp Val Thr Asp Ala Ser Asn<br>275 280 285 | | 864 |
| gaa gat gga gca ttt ctg caa caa tgg tct tat agt ggt aat gag aac<br>Glu Asp Gly Ala Phe Leu Gln Gln Trp Ser Tyr Ser Gly Asn Glu Asn<br>290 295 300 | | 912 |
| caa cag ttt gat ttt gag cat ctc gaa aat aat gtt tat aaa att act<br>Gln Gln Phe Asp Phe Glu His Leu Glu Asn Asn Val Tyr Lys Ile Thr<br>305 310 315 320 | | 960 |
| aat aaa aaa agt gga aaa tct ttg gat gtt tat aat ttt ggg act gag<br>Asn Lys Lys Ser Gly Lys Ser Leu Asp Val Tyr Asn Phe Gly Thr Glu<br>325 330 335 | | 1008 |
| aat ggt gtt aga atc caa cag tgg tca tat gga ggg gct cgc aat cag<br>Asn Gly Val Arg Ile Gln Gln Trp Ser Tyr Gly Gly Ala Arg Asn Gln<br>340 345 350 | | 1056 |
| cag ttt act gta caa agt gtt ggt gat ggt tat tat aag att att cca<br>Gln Phe Thr Val Gln Ser Val Gly Asp Gly Tyr Tyr Lys Ile Ile Pro<br>355 360 365 | | 1104 |
| cgc ggc agt gga aag tta gtg gaa gta gca gat ttt agt aaa gat gca<br>Arg Gly Ser Gly Lys Leu Val Glu Val Ala Asp Phe Ser Lys Asp Ala<br>370 375 380 | | 1152 |
| gga ggg aag ata caa caa tgg tct gat aac aac caa tta tct gga cag<br>Gly Gly Lys Ile Gln Gln Trp Ser Asp Asn Asn Gln Leu Ser Gly Gln<br>385 390 395 400 | | 1200 |
| tgg aaa ctt att aaa agt aaa agt tat tct aaa tta att cag gca gaa<br>Trp Lys Leu Ile Lys Ser Lys Ser Tyr Ser Lys Leu Ile Gln Ala Glu<br>405 410 415 | | 1248 |
| agt tat ttt gat tcc tca aaa gta caa ttg gaa gat acc tca gat gta<br>Ser Tyr Phe Asp Ser Ser Lys Val Gln Leu Glu Asp Thr Ser Asp Val<br>420 425 430 | | 1296 |
| gga ggt ggg aag aat gtt aaa tgt gat aat gaa gga gcc tgg atg gct<br>Gly Gly Gly Lys Asn Val Lys Cys Asp Asn Glu Gly Ala Trp Met Ala<br>435 440 445 | | 1344 |
| tat aag gat att gat ttc ccc agt tca ggt aat tat cga ata gaa tac<br>Tyr Lys Asp Ile Asp Phe Pro Ser Ser Gly Asn Tyr Arg Ile Glu Tyr<br>450 455 460 | | 1392 |
| aga gta gca agt gaa cgt gca gga gga aag ctg tct ctg gat ttg aat<br>Arg Val Ala Ser Glu Arg Ala Gly Gly Lys Leu Ser Leu Asp Leu Asn<br>465 470 475 480 | | 1440 |
| gca ggc tct ata gtt ctt ggc atg ctg gat gtt cct tca aca gga gga<br>Ala Gly Ser Ile Val Leu Gly Met Leu Asp Val Pro Ser Thr Gly Gly<br>485 490 495 | | 1488 |
| tgg cag aag tgg acc acc att tcc cat aca gtg aat gtg gat tca ggt<br>Trp Gln Lys Trp Thr Thr Ile Ser His Thr Val Asn Val Asp Ser Gly<br>500 505 510 | | 1536 |
| aca tat aac ttg ggg atc tat gtt caa cga gcc agc tgg aat atc aac<br>Thr Tyr Asn Leu Gly Ile Tyr Val Gln Arg Ala Ser Trp Asn Ile Asn<br>515 520 525 | | 1584 |
| tgg ata aag att aca aaa ata cct gaa cag tca aat ttg aat caa ggg<br>Trp Ile Lys Ile Thr Lys Ile Pro Glu Gln Ser Asn Leu Asn Gln Gly<br>530 535 540 | | 1632 |
| cgt cgt aat tct aaa tta att cag gca gaa agt tat ttt agt tac tca<br>Arg Arg Asn Ser Lys Leu Ile Gln Ala Glu Ser Tyr Phe Ser Tyr Ser<br>545 550 555 560 | | 1680 |
| gaa gta caa ctg gaa gat acc tta gat gta gga ggt gga aag aat gtt<br>Glu Val Gln Leu Glu Asp Thr Leu Asp Val Gly Gly Gly Lys Asn Val<br>565 570 575 | | 1728 |

-continued

```
aaa tgt gat aaa gaa ggg gcc tgg atg gct tac aag gat att gat ttc    1776
Lys Cys Asp Lys Glu Gly Ala Trp Met Ala Tyr Lys Asp Ile Asp Phe
        580                 585                 590 ccc agt tca gga agt tat cga gta gaa tac aga gtg gca agt gaa cgt    1824
Pro Ser Ser Gly Ser Tyr Arg Val Glu Tyr Arg Val Ala Ser Glu Arg
            595                 600                 605 gca gga gga aag ctg tcc cta gat ttg aat gca ggc tct ata gtg ctt    1872
Ala Gly Gly Lys Leu Ser Leu Asp Leu Asn Ala Gly Ser Ile Val Leu
        610                 615                 620 ggc atg ctg gat att cct tca aca gga gga ttg cag aag tgg acc acc    1920
Gly Met Leu Asp Ile Pro Ser Thr Gly Gly Leu Gln Lys Trp Thr Thr
625                 630                 635                 640 gcc agt tgg aat atc aat tgg att aga att aca aaa gtg gcg gcc gct    1968
Ala Ser Trp Asn Ile Asn Trp Ile Arg Ile Thr Lys Val Ala Ala Ala
                645                 650                 655 cga ggt cac cca ttc gaa ggt aag cct atc cct aac cct ctc ctc ggt    2016
Arg Gly His Pro Phe Glu Gly Lys Pro Ile Pro Asn Pro Leu Leu Gly
            660                 665                 670 ctc gat tct acg cgt acc ggt cat cat cac cat cac cat tga t          2059
Leu Asp Ser Thr Arg Thr Gly His His His His His His
        675                 680                 685

<210> SEQ ID NO 2
<211> LENGTH: 685
<212> TYPE: PRT
<213> ORGANISM: Tachypleus tridentatus

<400> SEQUENCE: 2

Met Leu Val Leu Leu Cys Cys Val Val Leu His Val Gly Val Ala Arg
1               5                   10                  15

Ile Cys Cys Ser His Glu Pro Lys Trp Gln Leu Val Trp Ser Asp Glu
            20                  25                  30

Phe Thr Asn Gly Ile Ser Ser Asp Trp Glu Phe Glu Met Gly Asn Gly
        35                  40                  45

Leu Asn Gly Trp Gly Asn Asn Glu Leu Gln Tyr Tyr Arg Arg Glu Asn
    50                  55                  60

Ala Gln Val Glu Gly Gly Lys Leu Val Ile Thr Ala Lys Arg Glu Asp
65                  70                  75                  80

Tyr Asp Gly Phe Lys Tyr Thr Ser Ala Arg Leu Lys Thr Gln Phe Asp
                85                  90                  95

Lys Ser Trp Lys Tyr Gly Lys Ile Glu Ala Lys Met Ala Ile Pro Ser
            100                 105                 110

Phe Arg Gly Val Trp Val Met Phe Trp Met Ser Gly Asp Asn Thr Asn
        115                 120                 125

Tyr Val Arg Trp Pro Ser Ser Gly Glu Ile Asp Phe Ile Glu His Arg
    130                 135                 140

Asn Thr Asn Asn Glu Lys Val Arg Gly Thr Ile His Trp Ser Thr Pro
145                 150                 155                 160

Asp Gly Ala His Ala His His Asn Arg Glu Ser Asn Thr Asn Gly Ile
                165                 170                 175

Asp Tyr His Ile Tyr Ser Val Glu Trp Asn Ser Ser Ile Val Lys Trp
            180                 185                 190

Phe Val Asn Gly Asn Gln Tyr Phe Glu Val Lys Ile Gln Gly Gly Val
        195                 200                 205

Asn Gly Lys Ser Ala Phe Arg Asn Lys Val Phe Val Ile Leu Asn Met
    210                 215                 220
```

-continued

```
Ala Ile Gly Gly Asn Trp Pro Gly Phe Asp Val Ala Asp Glu Ala Phe
225                 230                 235                 240

Pro Ala Lys Met Tyr Ile Asp Tyr Val Arg Val Tyr Gln Asp Ala Ser
            245                 250                 255

Thr Ser Ser Pro Val Gly Asp Thr Ser Leu Asp Gly Tyr Tyr Phe Val
        260                 265                 270

Gln Asn Arg His Ser Glu Leu Tyr Leu Asp Val Thr Asp Ala Ser Asn
    275                 280                 285

Glu Asp Gly Ala Phe Leu Gln Gln Trp Ser Tyr Ser Gly Asn Glu Asn
290                 295                 300

Gln Gln Phe Asp Phe Glu His Leu Glu Asn Asn Val Tyr Lys Ile Thr
305                 310                 315                 320

Asn Lys Lys Ser Gly Lys Ser Leu Asp Val Tyr Asn Phe Gly Thr Glu
            325                 330                 335

Asn Gly Val Arg Ile Gln Gln Trp Ser Tyr Gly Gly Ala Arg Asn Gln
        340                 345                 350

Gln Phe Thr Val Gln Ser Val Gly Asp Gly Tyr Tyr Lys Ile Ile Pro
    355                 360                 365

Arg Gly Ser Gly Lys Leu Val Glu Val Ala Asp Phe Ser Lys Asp Ala
370                 375                 380

Gly Gly Lys Ile Gln Gln Trp Ser Asp Asn Gln Leu Ser Gly Gln
385                 390                 395                 400

Trp Lys Leu Ile Lys Ser Lys Ser Tyr Ser Lys Leu Ile Gln Ala Glu
            405                 410                 415

Ser Tyr Phe Asp Ser Ser Lys Val Gln Leu Glu Asp Thr Ser Asp Val
        420                 425                 430

Gly Gly Gly Lys Asn Val Lys Cys Asp Asn Glu Gly Ala Trp Met Ala
    435                 440                 445

Tyr Lys Asp Ile Asp Phe Pro Ser Ser Gly Asn Tyr Arg Ile Glu Tyr
450                 455                 460

Arg Val Ala Ser Glu Arg Ala Gly Gly Lys Leu Ser Leu Asp Leu Asn
465                 470                 475                 480

Ala Gly Ser Ile Val Leu Gly Met Leu Asp Val Pro Ser Thr Gly Gly
            485                 490                 495

Trp Gln Lys Trp Thr Thr Ile Ser His Thr Val Asn Val Asp Ser Gly
        500                 505                 510

Thr Tyr Asn Leu Gly Ile Tyr Val Gln Arg Ala Ser Trp Asn Ile Asn
    515                 520                 525

Trp Ile Lys Ile Thr Lys Ile Pro Glu Gln Ser Asn Leu Asn Gln Gly
530                 535                 540

Arg Arg Asn Ser Lys Leu Ile Gln Ala Glu Ser Tyr Phe Ser Tyr Ser
545                 550                 555                 560

Glu Val Gln Leu Glu Asp Thr Leu Asp Val Gly Gly Lys Asn Val
            565                 570                 575

Lys Cys Asp Lys Glu Gly Ala Trp Met Ala Tyr Lys Asp Ile Asp Phe
        580                 585                 590

Pro Ser Ser Gly Ser Tyr Arg Val Glu Tyr Arg Val Ala Ser Glu Arg
    595                 600                 605

Ala Gly Gly Lys Leu Ser Leu Asp Leu Asn Ala Gly Ser Ile Val Leu
610                 615                 620

Gly Met Leu Asp Ile Pro Ser Thr Gly Gly Leu Gln Lys Trp Thr Thr
625                 630                 635                 640

Ala Ser Trp Asn Ile Asn Trp Ile Arg Ile Thr Lys Val Ala Ala Ala
```

-continued

```
                    645                 650                 655
    Arg Gly His Pro Phe Glu Gly Lys Pro Ile Pro Asn Pro Leu Leu Gly
                660                 665                 670
    Leu Asp Ser Thr Arg Thr Gly His His His His His
            675                 680                 685

<210> SEQ ID NO 3
<211> LENGTH: 1879
<212> TYPE: DNA
<213> ORGANISM: Tachypleus tridentatus
<220> FEATURE:
<221> NAME/KEY: CDS
<222> LOCATION: (1)..(930)

<400> SEQUENCE: 3 atg gat atc agt ttc ctg gtt ttt atc aca ctg tct atg gct ctc ttc       48
Met Asp Ile Ser Phe Leu Val Phe Ile Thr Leu Ser Met Ala Leu Phe
1               5                   10                  15 tcg agc aac gtg aca gga acg tca gta aca tca agg gta cga cgt gga       96
Ser Ser Asn Val Thr Gly Thr Ser Val Thr Ser Arg Val Arg Arg Gly
                20                  25                  30 ata aat gaa aaa cat tgt ggg ttc cga cca gta att aca aga att att      144
Ile Asn Glu Lys His Cys Gly Phe Arg Pro Val Ile Thr Arg Ile Ile
            35                  40                  45 ggt gga gga ata gcg acg cct cat tca tgg ccg tgg atg gtt gga att      192
Gly Gly Gly Ile Ala Thr Pro His Ser Trp Pro Trp Met Val Gly Ile
        50                  55                  60 ttc aaa gta aat cct cac cgt ttc ctt tgt ggt gga tct att att aat      240
Phe Lys Val Asn Pro His Arg Phe Leu Cys Gly Gly Ser Ile Ile Asn
65                  70                  75                  80 aaa gtc tct gtt gtt act gcc gcc cat tgt ctt gtg acg cag ttt gga      288
Lys Val Ser Val Val Thr Ala Ala His Cys Leu Val Thr Gln Phe Gly
                85                  90                  95 aac aga cag aat tat tct atc ttc gta aga gtt gga gcc cat gac ata      336
Asn Arg Gln Asn Tyr Ser Ile Phe Val Arg Val Gly Ala His Asp Ile
                100                 105                 110 gac aat tcg ggt aca aat tat caa gtg gat aaa gtt att gtt cac cag      384
Asp Asn Ser Gly Thr Asn Tyr Gln Val Asp Lys Val Ile Val His Gln
            115                 120                 125 ggc tac aaa cac cat tca cac tac tac gat atc ggt ttg att tta ctc      432
Gly Tyr Lys His His Ser His Tyr Tyr Asp Ile Gly Leu Ile Leu Leu
        130                 135                 140 tcg aaa cca gtc gaa tac aac gac aaa ata cag cct gtc tgt att cct      480
Ser Lys Pro Val Glu Tyr Asn Asp Lys Ile Gln Pro Val Cys Ile Pro
145                 150                 155                 160 gag ttc aac aaa cct cac gtg aac ttg aac aat att aag gtc gtc att      528
Glu Phe Asn Lys Pro His Val Asn Leu Asn Asn Ile Lys Val Val Ile
                165                 170                 175 act ggt tgg ggt gtt act ggg aaa gct act gag aaa cgt aac gtt ctt      576
Thr Gly Trp Gly Val Thr Gly Lys Ala Thr Glu Lys Arg Asn Val Leu
                180                 185                 190 cgt gaa ttg gag ttg ccc gtg gtt aca aac gaa cag tgc aac aaa tct      624
Arg Glu Leu Glu Leu Pro Val Val Thr Asn Glu Gln Cys Asn Lys Ser
            195                 200                 205 tat cag aca ctc cca ttc tca aaa ttg aac cga gga atc act aac gac      672
Tyr Gln Thr Leu Pro Phe Ser Lys Leu Asn Arg Gly Ile Thr Asn Asp
        210                 215                 220 atg att tgt gcg ggg ttt ccg gaa gga ggg aaa gat gct tgt cag ggc      720
Met Ile Cys Ala Gly Phe Pro Glu Gly Gly Lys Asp Ala Cys Gln Gly
225                 230                 235                 240
```

```
gac tct ggt ggt ccc ctg atg tat cag aat cca aca aca gga aga gtg      768
Asp Ser Gly Gly Pro Leu Met Tyr Gln Asn Pro Thr Thr Gly Arg Val
            245                 250                 255 aaa ata gtt gga gtt gta tca ttt ggg ttc gaa tgt gct cgt ccc aac      816
Lys Ile Val Gly Val Val Ser Phe Gly Phe Glu Cys Ala Arg Pro Asn
            260                 265                 270 ttc ccc ggt gtt tac acg cgc ctc tcg agc tac gtt aac tgg ctc cag      864
Phe Pro Gly Val Tyr Thr Arg Leu Ser Ser Tyr Val Asn Trp Leu Gln
            275                 280                 285 gaa atc acc ttc gga cag tca ctc gct tct tta ttt gaa gtt gta cca      912
Glu Ile Thr Phe Gly Gln Ser Leu Ala Ser Leu Phe Glu Val Val Pro
            290                 295                 300 ata ttt ata ccc gag tga gactgaagat aaatattgaa gagaaatcta             960
Ile Phe Ile Pro Glu
305 gaataatgta caatataaga agcctgaaat tactgaaata gaaaggcgcg tgatgagaaa   1020 tacgtttcaa attttatttt ttattaactt tattgtgttt aactattctt tacgtgggac   1080 atgaaatata aatctttatt tcttctttat atactttaga ttttcatttc atctatcttt   1140 atcagttttg taatgttact aataatattt cttatggcac ggatcgagcc tcgtgaatca   1200 cagtaaataa taataattat aaaatcacac attattaaaa gcaatagcat tcagagtgag   1260 taacatataa acttcactat gagtggactt ttttattcac attttaagtt cattactaac   1320 tgttgggagg tctttatatt gttgtatatt tatatattaa ttaggttggt ttagtacatt   1380 gttgttaatg gtggaatagg gcgtaggttt taaatgtgtt tgcaaaaaaa caaacaaaac   1440 aagtaatggt ggatgatggt tccaaagtaa ccgaagaac actttgaaca tttttataca   1500 aaaatttatg ttttaaaata cgagtatata caatcgatct ctaagtacaa gaaaaactga   1560 agtgttcatt caggtttaac agtgcaactt aaatcaacag ttagttgttc actaaacatt   1620 acaatttgat cctttataaa cgctaatact gtttaaacag tcagtaataa tacagtatca   1680 tagcatatca tatatgaagg tattttaaca ttctatatac aaagccagaa ttgaaaacgg   1740 taatattttg tacgattagt gaattattgt ttttaagaac aaactggtat caaatttaaa   1800 atatgaatct gtgatttaat attttttaca acgttctaac ttaccacttt tgttgtgaat   1860 aaaggtgttt acaaatgga                                                1879
```

<210> SEQ ID NO 4
<211> LENGTH: 309
<212> TYPE: PRT
<213> ORGANISM: Tachypleus tridentatus

<400> SEQUENCE: 4

```
Met Asp Ile Ser Phe Leu Val Phe Ile Thr Leu Ser Met Ala Leu Phe
1               5                   10                  15

Ser Ser Asn Val Thr Gly Thr Ser Val Thr Ser Arg Val Arg Arg Gly
            20                  25                  30

Ile Asn Glu Lys His Cys Gly Phe Arg Pro Val Ile Thr Arg Ile Ile
        35                  40                  45

Gly Gly Gly Ile Ala Thr Pro His Ser Trp Pro Trp Met Val Gly Ile
    50                  55                  60

Phe Lys Val Asn Pro His Arg Phe Leu Cys Gly Gly Ser Ile Ile Asn
65                  70                  75                  80

Lys Val Ser Val Val Thr Ala Ala His Cys Leu Val Thr Gln Phe Gly
                85                  90                  95

Asn Arg Gln Asn Tyr Ser Ile Phe Val Arg Val Gly Ala His Asp Ile
```

-continued

```
                    100                 105                 110
Asp Asn Ser Gly Thr Asn Tyr Gln Val Asp Lys Val Ile Val His Gln
                115                 120                 125
Gly Tyr Lys His His Ser His Tyr Tyr Asp Ile Gly Leu Ile Leu Leu
            130                 135                 140
Ser Lys Pro Val Glu Tyr Asn Asp Lys Ile Gln Pro Val Cys Ile Pro
145                 150                 155                 160
Glu Phe Asn Lys Pro His Val Asn Leu Asn Asn Ile Lys Val Val Ile
                165                 170                 175
Thr Gly Trp Gly Val Thr Gly Lys Ala Thr Glu Lys Arg Asn Val Leu
            180                 185                 190
Arg Glu Leu Glu Leu Pro Val Val Thr Asn Glu Gln Cys Asn Lys Ser
            195                 200                 205
Tyr Gln Thr Leu Pro Phe Ser Lys Leu Asn Arg Gly Ile Thr Asn Asp
            210                 215                 220
Met Ile Cys Ala Gly Phe Pro Glu Gly Gly Lys Asp Ala Cys Gln Gly
225                 230                 235                 240
Asp Ser Gly Gly Pro Leu Met Tyr Gln Asn Pro Thr Thr Gly Arg Val
                245                 250                 255
Lys Ile Val Gly Val Val Ser Phe Gly Phe Glu Cys Ala Arg Pro Asn
            260                 265                 270
Phe Pro Gly Val Tyr Thr Arg Leu Ser Ser Tyr Val Asn Trp Leu Gln
            275                 280                 285
Glu Ile Thr Phe Gly Gln Ser Leu Ala Ser Leu Phe Glu Val Val Pro
            290                 295                 300
Ile Phe Ile Pro Glu
305

<210> SEQ ID NO 5
<211> LENGTH: 22
<212> TYPE: DNA
<213> ORGANISM: Artificial
<220> FEATURE:
<223> OTHER INFORMATION: Primer for sequencing

<400> SEQUENCE: 5
tggagataat taaaatgata ac                                              22

<210> SEQ ID NO 6
<211> LENGTH: 18
<212> TYPE: DNA
<213> ORGANISM: Artificial
<220> FEATURE:
<223> OTHER INFORMATION: Primer for sequencing

<400> SEQUENCE: 6
gtgcaaactc ctttactt                                                   18

<210> SEQ ID NO 7
<211> LENGTH: 20
<212> TYPE: DNA
<213> ORGANISM: Artificial
<220> FEATURE:
<223> OTHER INFORMATION: Primer for sequencing

<400> SEQUENCE: 7
caatgaaaaa gtcagaggaa                                                 20

<210> SEQ ID NO 8
```

<211> LENGTH: 20
<212> TYPE: DNA
<213> ORGANISM: Artificial
<220> FEATURE:
<223> OTHER INFORMATION: Primer for sequencing

<400> SEQUENCE: 8
ataatgttta taaaattact                                               20

<210> SEQ ID NO 9
<211> LENGTH: 20
<212> TYPE: DNA
<213> ORGANISM: Artificial
<220> FEATURE:
<223> OTHER INFORMATION: Primer for sequencing

<400> SEQUENCE: 9
agattacaaa aatacctgaa                                               20

<210> SEQ ID NO 10
<211> LENGTH: 20
<212> TYPE: DNA
<213> ORGANISM: Artificial
<220> FEATURE:
<223> OTHER INFORMATION: Primer for sequencing

<400> SEQUENCE: 10
aacaaaccat ttaacaatgg                                               20

<210> SEQ ID NO 11
<211> LENGTH: 20
<212> TYPE: DNA
<213> ORGANISM: Artificial
<220> FEATURE:
<223> OTHER INFORMATION: Primer for sequencing

<400> SEQUENCE: 11
tcaccaacac tttgtacagt                                               20

<210> SEQ ID NO 12
<211> LENGTH: 20
<212> TYPE: DNA
<213> ORGANISM: Artificial
<220> FEATURE:
<223> OTHER INFORMATION: Primer for sequencing

<400> SEQUENCE: 12
tgatattcca gctggctcgt                                               20

<210> SEQ ID NO 13
<211> LENGTH: 20
<212> TYPE: DNA
<213> ORGANISM: Artificial
<220> FEATURE:
<223> OTHER INFORMATION: Primer for sequencing

<400> SEQUENCE: 13
agttactcag aagtacaact                                               20

<210> SEQ ID NO 14
<211> LENGTH: 22
<212> TYPE: DNA
<213> ORGANISM: Artificial
<220> FEATURE:
<223> OTHER INFORMATION: PCR primer

<400> SEQUENCE: 14

```
ctgcgagcag ttgtttgttg tt                                              22

<210> SEQ ID NO 15
<211> LENGTH: 20
<212> TYPE: DNA
<213> ORGANISM: Artificial
<220> FEATURE:
<223> OTHER INFORMATION: PCR primer

<400> SEQUENCE: 15
cgcacagaat ctagcgctta                                                 20

<210> SEQ ID NO 16
<211> LENGTH: 22
<212> TYPE: DNA
<213> ORGANISM: Artificial
<220> FEATURE:
<223> OTHER INFORMATION: PCR primer

<400> SEQUENCE: 16
ctgcgagcag ttgtttgttg tt                                              22

<210> SEQ ID NO 17
<211> LENGTH: 20
<212> TYPE: DNA
<213> ORGANISM: Artificial
<220> FEATURE:
<223> OTHER INFORMATION: PCR primer

<400> SEQUENCE: 17
cgcacagaat ctagcgctta                                                 20

<210> SEQ ID NO 18
<211> LENGTH: 22
<212> TYPE: DNA
<213> ORGANISM: Artificial
<220> FEATURE:
<223> OTHER INFORMATION: Primer for sequencing

<400> SEQUENCE: 18
tggagataat taaaatgata ac                                              22

<210> SEQ ID NO 19
<211> LENGTH: 18
<212> TYPE: DNA
<213> ORGANISM: Artificial
<220> FEATURE:
<223> OTHER INFORMATION: Primer for sequencing

<400> SEQUENCE: 19
gtgcaaactc ctttactt                                                   18
```

METHOD FOR PRODUCING FACTOR G DERIVED FROM HORSESHOE CRAB

RELATED APPLICATIONS

This application is a divisional of application Ser. No. 11/387,443 now U.S. Pat. No. 7,541,162 filed on Mar. 23, 2006 which claims priority to U.S. Provisional Application No. 60/665,779, filed Mar. 28, 2005, both of which are incorporated herein by reference.

FIELD OF THE INVENTION

The present invention relates to a virus harboring DNA encoding a subunit of factor G derived from a horseshoe crab (hereinafter may be referred to as *limulus*-derived factor G), to a cell harboring the virus, and to a method of producing factor G by use of the cell.

BACKGROUND ART

Abbreviations used in the present specification are as follows.

AcNPV: nuclear polyhedrosis virus of *Autographa californica*
BG: (1→3)-β-D-glucan
Et: endotoxin (also referred to as lipopolysaccharide)
HEPES: 2-[4-(2-hydroxyethyl)-1-piperazinyl]ethanesulfonic acid
HRP: horseradish peroxidase
MOI: multiplicity of infection
NPV: nuclear polyhedrosis virus
PBS: phosphate buffered saline
PCR: polymerase chain reaction
pNA: p-nitroaniline
PVDF: polyvinylidene difluoride
SDS: sodium dodecyl sulfate
SDS-PAGE: sodium dodecyl sulfate-polyacrylamide gel electrophoresis Japanese Patent Application laid-Open (kokai) No. 08-122334 and a non-patent document (J. Protein Chem., 5, p. 255-268 (1986)) disclose methods for determining Et or BG by use of an amebocyte lysate of a horseshoe crab (hereinafter referred to simply as a lysate). These methods are based on coagulation of the lysate by Et or BG. The coagulation reaction occurs through cascade reaction of coagulation factors.

For example, when BG is brought into contact with the lysate, factor G contained in the lysate is activated, to thereby form activated factor G. The activated factor G activates a pro-clotting enzyme present in the lysate, to thereby form a clotting enzyme. The clotting enzyme hydrolyzes a specific site of a coagulogen molecule present in the lysate, thereby forming coagulin gel, leading to coagulation of the lysate. The coagulogen also acts on a synthetic substrate (e.g., t-butoxycarbonyl-leucyl-glycyl-arginine-pNA (Boc-Leu-Gly-Arg-pNA)), to thereby hydrolyze the amide bonds, whereby pNA is released. Thus, BG can be determined through measuring absorbance of the formed coloring substance (pNA) (disclosed in Japanese Patent Application laid-Open (kokai) No. 08-122334).

Factor G is a protein formed of subunits α and β, and cloning of each subunit has already been performed (disclosed in J. Biol. Chem., 269(2), p. 1370-1374 (1994)). However, an active protein (factor G) has been difficult to express through employment of cloned DNAs encoding the subunits.

SUMMARY OF THE INVENTION

Thus, an object of the present invention is provide an virus harboring a DNA encoding a subunit of *limulus*-derived factor G, the virus being capable of mass-producing a BG assay reagent of satisfactory quality, steadily and at low cost. Another object is to provide a cell harboring the virus. Still another object is to provide a method of producing factor G by use of the cell.

The present inventors have conducted extensive studies in order to attain the aforementioned objects, and have found that a protein having factor G activity can be produced by use of a cell harboring a virus containing a DNA encoding a subunit of factor G, whereby a BG assay reagent of satisfactory quality can be mass-produced steadily and at low cost. The present invention has been accomplished on the basis of this finding.

Accordingly, the present invention provides a virus harboring a DNA encoding subunit α of *limulus*-derived factor G (hereinafter the virus may be referred to as "virus 1 of the present invention"). The horseshoe crab (*limulus*) is preferably selected from among *Tachypleus tridentatus, Limulus polyphemus, Tachypleus gigas*, and *Carcinoscorpius rotundicauda*.

The DNA encoding subunit α of *limulus*-derived factor G is preferably a DNA (A) or a DNA (B) as described below:

(A) a DNA encoding a protein having an amino acid sequence defined by SEQ ID NO: 2, (B) a DNA encoding a protein having an amino acid sequence defined by SEQ ID NO: 2 in which one or more amino acid residues are deleted, substituted, inserted, or transposed and having activity of subunit α of *limulus*-derived factor G.

The DNA encoding subunit α of *limulus*-derived factor G herein is also preferably a DNA (a) or a DNA (b) as described below:

(a) a DNA having a nucleotide sequence defined by nucleotides 1 to 2022 in SEQ ID NO: 1, (b) a DNA having a nucleotide mutation in a nucleotide sequence defined by nucleotides 1 to 2022 in SEQ ID NO: 1, the mutation causing deletion, substitution, insertion, or transposition of one or more amino acid residues in the amino acid sequence of a protein encoded by the mutation-containing nucleotide sequence, and the expressed protein having activity of subunit α of *limulus*-derived factor G.

The virus is preferably baculovirus. The baculovirus is preferably NPV. The NPV is preferably AcNPV.

The present invention also provides a virus harboring a DNA encoding subunit β of *limulus*-derived factor G (hereinafter the virus may be referred to as "virus 2 of the present invention").

The horseshoe crab (*limulus*) is preferably selected from among *Tachypleus tridentatus, Limulus polyphemus, Tachypleus gigas*, and *Carcinoscorpius rotundicauda*.

The DNA encoding subunit β of *limulus*-derived factor G herein is also preferably a DNA (A) or a DNA (B) as described below:

(A) a DNA encoding a protein having an amino acid sequence defined by SEQ ID NO: 4, (B) a DNA encoding a protein having an amino acid sequence defined by SEQ ID NO: 4 in which one or more amino acid residues are deleted, substituted, inserted, or transposed and having activity of subunit β of *limulus*-derived factor G.

The DNA encoding subunit β of *limulus*-derived factor G herein is also preferably a DNA (a) or a DNA (b) as described below:

(a) a DNA having a nucleotide sequence defined by nucleotides 1 to 930 in SEQ ID NO: 3, (b) a DNA having a nucleotide mutation in a nucleotide sequence defined by nucleotides 1 to 930 in SEQ ID NO: 3, the mutation causing deletion, substitution, insertion, or transposition of one or more amino acid residues in the amino acid sequence of a protein encoded by the mutation-containing nucleotide sequence, and the expressed protein having activity of subunit β of *limulus*-derived factor G.

The virus is preferably baculovirus. The baculovirus is preferably NPV. The NPV is preferably AcNPV.

Hereinafter, virus 1 of the present invention and virus 2 of the present invention may be collectively or individually referred to as "the virus of the present invention".

The present invention also provides a cell harboring the virus of the present invention (hereinafter the cell may be referred to as "the cell of the present invention").

The cell of the present invention preferably harbors viruses 1 and 2 of the present invention. Preferably, the cell is obtained through infection with virus 1 and virus 2 such that MOI of virus 1 exceeds MOI of virus 2. In this case, the ratio of MOI of virus 1 to MOI of virus 2 is preferably controlled to 1.5:1 to 64:1.

The cell of the present invention is preferably a cell of insect origin.

The present invention also provides a method of producing subunit α and/or subunit β of *limulus*-derived factor G, the method comprising growing the cell of the present invention and collecting subunit α and/or subunit β of *limulus*-derived factor G from the growth product (hereinafter the method may be referred to as "the method of the present invention"). The subunit α and/or subunit β of *limulus*-derived factor G is preferably a protein which is formed of subunit α and subunit β and which maintains *limulus*-derived factor G activity.

The method of the present invention includes a concept of "a method of producing factor G, the method comprising growing a cell which harbors a DNA encoding subunit α of factor G derived from a horseshoe crab and a DNA encoding subunit β of factor G derived from a horseshoe crab, and collecting, from the growth product, a protein having activity of factor G derived from a horseshoe crab".

The virus of the present invention is very useful, since the cell of the present invention, which is useful for mass-producing factor G of satisfactory quality, steadily, at high efficiency and low cost, can be attained by using the virus.

Employment of the cell is remarkably useful, since a protein which maintains factor G activity and which has satisfactory quality can be mass-produced steadily at high efficiency and low cost, whereby the method of the present invention can be attained. Furthermore, through employment of the method of the present invention, a protein which maintains factor G activity and which has satisfactory quality can be mass-produced steadily, at high efficiency and low cost.

DETAILED DESCRIPTION OF PREFERRED EMBODIMENTS

Best modes for carrying out the present invention will next be described in detail.

<1>-1 Virus 1 of the Present Invention

Virus 1 of the present invention is a virus harboring a DNA encoding subunit α of *limulus*-derived factor G.

No particular limitation is imposed on the type of the DNA encoding subunit α of *limulus*-derived factor G harbored by virus 1 of the present invention, so long as the DNA encodes subunit α of *limulus*-derived factor G.

Examples of the DNA include those encoding subunit α of factor G derived from the following horseshoe crabs: *Tachypleus tridentatus, Limulus polyphemus, Tachypleus gigas*, and *Carcinoscorpius rotundicauda*.

Of these, DNAs encoding subunit α of factor G derived from *Tachypleus tridentatus* and *Limulus polyphemus* are preferred, more preferably a DNA encoding subunit α of factor G derived from *Tachypleus tridentatus*.

Particularly, the DNA harbored by virus 1 of the present invention is preferably the following DNA (A) or (B):

(A) a DNA encoding a protein having an amino acid sequence defined by SEQ ID NO: 2, (B) a DNA encoding a protein having an amino acid sequence defined by SEQ ID NO: 2 in which one or more amino acid residues are deleted, substituted, inserted, or transposed and having activity of subunit α of *limulus*-derived factor G.

The DNA encoding a protein having an amino acid sequence defined by SEQ ID NO: 2 herein is a DNA encoding subunit α of factor G derived from *Tachypleus tridentatus*.

The DNA coding for a naturally occurring protein may include polymorphism and mutations, and the formed protein may include mutations in the amino acid sequence due to intracellular alteration or modification incurred during purification; such as deletion, substitution, insertion, and transposition in amino acid residues. Although having such a mutation, some proteins are known to exhibit physiological and biological effects virtually the same as those of the protein having none of the above mutations. Thus, the protein encoded by DNA (B), which slightly differs from the protein encoded by DNA (A) in structure and which has no significant difference in function can be regarded as substantially equivalent to the protein encoded by DNA (A). A similar logic is also applied to the case where the aforementioned mutations are intentionally introduced into an amino acid sequence of protein. In this case, a wider range of variants can be fabricated. For example, a polypeptide engineered from human interleukin 2 (IL-2) so that a certain cysteine residue in the amino acid sequence of IL-2 is substituted by serine is known to maintain human interleukin 2 (IL-2) activity (Science, 224, 1431 (1984)). Also, a certain protein is known to have a peptide region that is not essential in terms of activity. Examples of such a protein include a signal peptide present in a protein secreted from a cell and a pro-sequence observed in a protease precursor or a similar substance. Most of these peptide regions are removed after translation or during conversion to the corresponding activated proteins. Although having different primary structures, the above-mentioned variants are virtually equivalent in terms of the function to the protein encoded by DNA (A). Therefore, the protein encoded by DNA (B) represents these proteins.

In the present specification, the term "one or more amino acid residues" refers to amino acid residues which are allowed to have mutations without impairing the protein activity. For example, when a protein contains 600 amino acid residues, the number of such amino acid residues is about 1 to 30, preferably 1 to 15, more preferably 1 to 8.

The protein encoded by DNA (B) has activity of subunit α of *limulus*-derived factor G. Since subunit α of factor G has BG-binding activity, subunit α activity can be detected by checking the presence of BG-binding activity.

The state "harboring a DNA" in virus 1 of the present invention does not exclude the state in which the virus harbors other nucleotides and DNAs, so long as the relevant DNA is harbored. Thus, in addition to the DNA, other DNAs encoding a marker peptide etc. may be harbored.

For example, a vector harboring a linked DNA between the aforementioned DNA (A) or (B) and a DNA encoding a marker peptide etc. also falls within the scope of virus 1 of the present invention. When the DNA to be harbored is designed in the above manner, a protein fused with a marker peptide etc. may be expressed. The thus-expressed protein is advantageous for facilitating purification, detection, analysis, etc. Examples of the marker peptide include protein A, an insulin signal sequence, His-tag, FLAG, CBP (calmodulin-binding protein), and GST (glutathione S-transferase). For example, a protein fused with protein A may be purified in a simple manner through affinity chromatography employing an IgG-immobilized solid phase. Similarly, a His-tag-fused protein may be purified with a magnetic nickel-immobilized solid phase, whereas a FLAG-fused protein may be purified with an anti-FLAG antibody-immobilized solid phase. A protein fused with an insulin signal sequence is secreted from a cell to the outside (e.g., culture medium). Therefore, an extraction step including crushing of cells may be eliminated.

No particular limitation is imposed on the production method of virus 1 of the present invention. One exemplary method of producing virus 1 of the present invention will be described as follows. More specific procedure thereof will be described in the Examples.

Firstly, a DNA encoding subunit α of *limulus*-derived factor G is provided. In the case where the aforementioned DNA (A) is employed as the DNA, a DNA encoding a protein having an amino acid sequence defined by SEQ ID NO: 2 is provided. In the case where the aforementioned DNA (B) is employed as the DNA, provided is a DNA encoding a protein having an amino acid sequence defined by SEQ ID NO: 2 in which one or more amino acid residues are deleted, substituted, inserted, or transposed and having activity of subunit α of *limulus*-derived factor G. No particular limitation is imposed on the type of the DNA, so long as the DNA encodes the relevant protein. The DNA includes those having a variety of nucleotide sequences due to degeneracy of genetic codes. However, any of these DNAs having a specific nucleotide sequence may be employed.

The DNA (A) serving as a DNA encoding a protein having an amino acid sequence defined by SEQ ID NO: 2 may be, among others, a DNA having a nucleotide sequence defined by nucleotides 1 to 2022 in SEQ ID NO: 1. Alternatively, a DNA deposited in GenBank with an accession No. D16622 may also be employed. Furthermore, a DNA having a nucleotide sequence defined by nucleotides 1 to 2058 in SEQ ID NO: 1 may also be employed.

The DNA (B) serving as a DNA encoding a protein having an amino acid sequence defined by SEQ ID NO: 2 in which one or more amino acid residues are deleted, substituted, inserted, or transposed and having activity of subunit α of *limulus*-derived factor G, may be the aforementioned DNA (A), a complementary DNA thereof, or a DNA which hybridizes with any of the DNAs under stringent conditions.

As used herein, the term "stringent conditions" refers to conditions which allow formation of a so-called specific hybrid but do not allow formation of a non-specific hybrid (see, for example, Sambrook, J. et al., Molecular Cloning A Laboratory Manual, second Edition, Cold Spring Harbor Laboratory Press (1989)). Specific examples of the stringent conditions include performing hybridization in a solution containing 50% formamide, 4×SSC, 50 mM HEPES (pH 7.0), 10×Denhardt's solution, and 100 µg/mL salmon sperm DNA at 42° C., and washing at room temperature with 2×SSC and a 0.1% SDS solution and at 50° C. with 0.1×SSC and a 0.1% SDS solution.

Through introduction of such a DNA into virus, virus 1 of the present invention can be produced.

No particular limitation is imposed on the species of the virus into which such a DNA is introduced, so long as the virus is available for transfection. The virus is preferably baculovirus. The baculovirus is preferably NPV. No particular limitation is imposed on the species of the NPV, so long as the NPV is a virus belonging to NPVs. For example, AcNPV or *Bombyx mori* NPV (BmNPV) may be employed. Of these, AcNPV is preferred.

Introduction of a DNA into virus may be performed through homologous recombination by use of a transfer vector. No particular limitation is imposed on the type of the transfer vector. For example, pPSC8 (Protein Science), pFastBac (Invitrogen), or pVL1393 (Pharmingen) may be employed. Of these, pPSC8 is preferred. These transfer vectors may be commercial products.

No particular limitation is imposed on the method of homologous recombination by use of a transfer vector. A specific example thereof will be described later in the Examples.

Whether or not the produced virus harbors the aforementioned DNA (A) or DNA (B) may be confirmed by any of the following procedures: checking that the produced virus harbors a DNA encoding subunit α of *limulus*-derived factor G through nucleotide sequence analysis; checking that a protein expressed by the produced virus has an amino acid sequence of subunit α of *limulus*-derived factor G; and checking that a protein expressed by the produced virus has activity of subunit α of *limulus*-derived factor G.

Virus 1 of the present invention may be used in the production of "the cell of the present invention" described later, and in "the method of the present invention."

<1>-2 Virus 2 of the Present Invention

Virus 2 of the present invention is a virus harboring a DNA encoding subunit β of *limulus*-derived factor G.

Examples of the horseshoe crab and preferred embodiments are the same as described in <1>-1.

Particularly, the DNA harbored by virus 2 of the present invention is preferably the following DNA (A) or (B):

(A) a DNA encoding a protein having an amino acid sequence defined by SEQ ID NO: 4, (B) a DNA encoding a protein having an amino acid sequence defined by SEQ ID NO: 4 in which one or more amino acid residues are deleted, substituted, inserted, or transposed and having activity of subunit β of *limulus*-derived factor G.

The DNA encoding a protein having an amino acid sequence defined by SEQ ID NO: 4 herein is a DNA encoding subunit β of factor G derived from *Tachypleus tridentatus*.

The definition of the protein encoded by DNA (B) is the same as described in <1>-1. The protein encoded by DNA (B) has activity of subunit β of *limulus*-derived factor G. Since subunit β of factor G has serine protease activity, subunit β activity can be confirmed by the presence of serine protease activity.

Notably, the term "one or more amino acid residues" and the state "harboring a DNA" are the same as described in <1>-1. The method of producing virus 2 of the present invention is identical to that described in <1>-1, except that SEQ ID NO: 2 is changed to SEQ ID NO: 4.

The DNA (A) serving as a DNA encoding a protein having an amino acid sequence defined by SEQ ID NO: 4 may be, among others, a DNA having a nucleotide sequence defined by nucleotides 1 to 930 in SEQ ID NO: 3. Alternatively, a DNA deposited in GenBank with an accession No. D16623 may also be employed.

The aforementioned DNA (B) encoding a protein having an amino acid sequence defined by SEQ ID NO: 4 in which one or more amino acid residues are deleted, substituted, inserted, or transposed and having activity of subunit β of *limulus*-derived factor G is the same as described in <1>-1.

Through introduction of such a DNA into virus, virus 2 of the present invention can be produced. Examples of the virus into which the DNA is introduced, preferred embodiments, and the DNA introduction method are the same as described in <1>-1.

Whether or not the produced virus harbors the aforementioned DNA (A) or DNA (B) may be confirmed through the same method as described in <1>-1.

Virus 2 of the present invention may be used in the production of "the cell of the present invention" described later, and in "the method of the present invention."

<2> The Cell of the Present Invention

The cell of the present invention harbors the virus of the present invention.

The virus of the present invention is the same as mentioned above.

No particular limitation is imposed on the cell to be employed, so long as the cell allows infection with the virus of the present invention, and can express, by the mediation of the virus of the present invention, subunits α and/or β of *limulus*-derived factor G. Examples of the cell include cells derived from insects, and specific examples include an Sf9 cell.

No particular limitation is imposed on the method for causing the virus of the present invention to harbor the cell. For example, contact between the virus of the present invention and the cell readily causes infection of the cell with the virus of the present invention, whereby the cell can harbor the virus of the present invention. A specific method thereof will be described later in the Examples.

The cell of present invention may harbor sole virus 1 of the present invention, sole virus 2 of the present invention, or both viruses 1 and 2 of the present invention. The cell may further harbor a virus other than viruses 1 and 2.

In the case where the cell of the present invention harbors viruses 1 and 2 of the present invention, the cell is preferably produced by infecting with the viruses 1 and 2 such that MOI of virus 1 exceeds MOI of virus 2. For example, the cell of the present invention may be infected with viruses 1 and 2 at a ratio of MOI of virus 1 to MOI of virus 2 of 1.5:1 to 64:1. The ratio of MOI of virus 1 to MOI of virus 2 is more preferably controlled to 1.5:1 to 32:1, 2:1 to 32:1, 2:1 to 16:1, 2:1 to 8:1, 2:1 to 6:1, 2:1 to 4:1 or 3:1 to 5:1, 4:1, in this order.

Since the cell of the present invention can produce subunits α and/or β of *limulus*-derived factor G, the cell of the present invention may be selected on the basis of the production performance as an index.

The cell of the present invention may be employed in, for example, the below-mentioned method of the present invention.

<3> The Method of the Present Invention

The method of the present invention for producing subunit α and/or subunit β of *limulus*-derived factor G includes growing the cell of the present invention and collecting subunit α and/or subunit β of *limulus*-derived factor G from the growth product.

The cell of the present invention is the same as mentioned above.

In the present invention, the term "grow" refers to a concept including proliferation of cells which are transformants and growing organisms such as animals and insects into which transformant cells have been incorporated. The term "growth product" is a concept including a culture medium (supernatant of the culture) after completion of growth of transformants, cultured cells themselves, and matter secreted or excreted from organisms such as animals and insects into which the cells have been incorporated.

No particular limitation is imposed on the growth conditions (e.g., medium and culture conditions), so long as the cell of the present invention can grow and produce subunit α and/or subunit β of *limulus*-derived factor G. The conditions are appropriately selected in accordance with the type of the vectors, cells, etc. employed. For example, culturing temperature may be about 20 to 40° C.

The growth period of the cell of the present invention may also be appropriately tuned in accordance with the amount of the cell used in the present invention, a desired production amount of the subunit(s), and other growth conditions.

The person skilled in the art may select the method for collecting subunit α and/or subunit β of *limulus*-derived factor G from the growth product from generally employed methods in accordance with the type of the growth product.

For example, in the case where these subunits are produced in the soluble form which are secreted into a culture medium (culture supernatant), the culture medium is collected and may be employed without performing further treatment. In the case where these subunits are produced in the soluble form which are secreted in the cytoplasm, or produced in the insoluble form (membrane-binding), these subunits may be extracted through extraction with cell crushing such as the nitrogen cavitation apparatus method, homogenizing, glass beads milling, sonication treatment, the permeation shock method, or freeze-thawing; extraction with a surfactant; or a combination thereof. The extract itself may be used as subunit α and/or subunit β without performing further treatment.

The method of the present invention may further include other steps, so long as the method includes growing the cell of the present invention and collecting subunit α and/or subunit β of *limulus*-derived factor G from the growth product. For example, the method may include a step of purifying the collected subunit(s). The purification may be incomplete (partial) purification or complete purification, and may be appropriately selected in accordance with the use purpose of the subunit(s).

Specific examples of the purification method include salting out by the mediation of a salt such as ammonium sulfate or sodium sulfate; centrifugation; dialysis; ultrafiltration; chromatographic methods such as adsorption chromatography, ion-exchange chromatography, hydrophobic chromatography, reverse-phase chromatography, gel filtration, gel permeation chromatography, and affinity chromatography; electrophoresis; and combinations thereof.

The method of the present invention may be employed for producing sole subunit α, sole subunit β, or both subunits α and β. The method may also produce a subunit other than subunits α and β.

In the production of subunit α, a cell harboring virus 1 of the present invention is employed. In the production of subunit β, a cell harboring virus 2 of the present invention is employed. In the production of subunits α and β, a cell harboring both viruses 1 and 2 of the present invention is employed.

In the case where both subunits α and β are produced, a protein which is formed of subunits α and β and which maintains activity of *limulus*-derived factor G can be produced.

Whether or not the produced protein is subunit α and/or subunit β, is formed of subunits α and β, or maintains activity of *limulus*-derived factor G may be confirmed through analysis of the collected protein such as amino acid sequence, molecular weight, electrophoresis features, Western blotting employing an antibody reacting specifically to the relevant subunit, BG binding performance, or presence of serine protease activity.

The method of the present invention realizes remarkably effective production of a protein which is formed of subunit α, subunit β, or subunits α and β and which maintains activity of *limulus*-derived factor G.

The method of the present invention includes a concept of "a method of producing factor G, the method comprising growing a cell which harbors a DNA encoding subunit α of factor G derived from a horseshoe crab and a DNA encoding subunit β of factor G derived from a horseshoe crab, and collecting, from the growth product, a protein having activity of factor G derived from a horseshoe crab".

EXAMPLES

The present invention will next be described in detail by way of examples.

<1> Expression of Subunit α of Factor G

A cDNA encoding factor G subunit α was kindly offered by Dr. Tatsushi MUTA (Department of Molecular and Cellular Biochemistry, Graduate School of Medical Sciences, Kyushu University). The cDNA had been prepared through a method disclosed in J. Biol. Chem., 269(2), p. 1370-1374 (1994). The cDNA was introduced into a transfer vector (pPSC8), and a clone having a predetermined nucleotide sequence was selected. The thus-selected expression vector (Factor G-α/pPSC8) DNA and a baculovirus (AcNPV) DNA were co-transfected into Sf9 cells. The virus fluid obtained from the culture supernatant was purified and amplified. The viral DNA was extracted from the cells infected with the baculovirus, and sequenced. Cells (expresSF+, trade name) were infected with the thus-obtained virus fluid, and the expression product was analyzed through Western blotting. Details of these steps will next be described.

1. Construction of Expression Vector

A cDNA encoding factor G subunit α (Factor G-α/pFastbac1) was treated with BamHIH/Hind III, and fragments (about 2,100 bp) having a target gene were collected. The sample was blunt-ended, and subsequently, ligated through mixing with Nru I-treated pPSC8 (product of Protein Science). *E. coli* JM109 was transformed with the ligation product, to thereby form a transformant. Plasmids in which fragments of the target size had been determined were purified, and sequenced. The sequencing was performed by use of the below-described primers and ABI Prism Big Dye Terminator Cycle Sequencing Kit Ver.3 (Applied Biosystems). Electrophoresis was performed by means of an automated sequencer ABI Prism 310 Genetic Analyzer (Applied Biosystems), and analysis was performed by means of Genetyx (Genetyx). Sequences of the primers are shown in the following sequence list by SEQ ID NOs: 5 to 13.

SEQ ID NO: 5: PSC F
SEQ ID NO: 6: PSC R
SEQ ID NO: 7: Factor G α 441/460-F
SEQ ID NO: 8: Factor G α 941/960-F
SEQ ID NO: 9: Factor G α 1601/1620-F
SEQ ID NO: 10: Factor G α 582/563-R
SEQ ID NO: 11: Factor G α 1082/1063-R
SEQ ID NO: 12: Factor G α 1582/1563-R
SEQ ID NO: 13: Factor G α 1700/1681-R A clone in which insertion of a target gene had been confirmed was inoculated to an LB medium (100 mL) containing 50 μg/mL ampicillin, and cultivated at 30° C. for one night. Proliferated cells were collected, and plasmids were purified in accordance with the manual of Plasmid Midi Kit (QIAGEN).

2. Co-transfection

To Sf9 cells (1.0×106) plated in a 25-cm2 flask was added a serum-free SF-900 II medium (product of Invitrogen) (200 μL) containing an expression vector harboring a cDNA encoding factor G subunit α (4.6 μg), a linear AcNPV DNA (85 ng), and LIPOFECTIN Reagent (product of Invitrogen) (5 μL). After the culture had been allowed to stand at 28° C. for six hours, a serum-free SF-900 II medium was further added so as to adjust the volume of the culture liquid to 5 mL. The culture was further cultivated at 28° C. for nine days, and the culture supernatant was collected. The thus-obtained solution through co-transfection referred to as a co-transfection solution.

3. Purification of Recombinant Virus

The recombinant virus was purified through the plaque assay method. The specific procedure is as follows.

Sf9 cells (2.0×106) were plated onto a plate (diameter: 60 mm) and allowed to stand at 28° C. for one hour, whereby the cells were adhered to the bottom surface. The aforementioned co-transfection solution was diluted with a serum-free Sf-900 II medium at dilution factors of 104, 105, 106, and 107. An aliquot (1 mL) of each of these diluted solutions was added to the cells, followed by gentle shaking at room temperature for one hour. After removal of the plate supernatant (virus fluid), a serum-free Sf-900 II medium (4 mL) containing 0.5% SeaKemGTG agarose (product of BMA) was added to the plate, and stationary culture was performed at 28° C. for seven days. From each culture medium, six plaques of infected insect cells including no polyhedra were collected. The plaques of each medium were suspended in a serum-free Sf-900 II medium (1 mL), to thereby serve as a virus fluid.

4. Amplification of Recombinant Virus

Next, amplification of the recombinant virus (preparation of recombinant virus fluid) was performed. The specific procedure is as follows.

To Sf9 cells (2.0×106) plated in a 25-cm2 flask was added each (0.5 mL) of the aforementioned virus fluids, followed by stationary cultivation at 28° C. for one hour. A serum-free SF-900 II medium was added to the culture so as to adjust the volume of the culture liquid to 5 mL, and the culture was further stationary-cultivated for three days, to thereby yield a first-generation virus fluid.

To Sf9 cells (6.0×106) plated in a 75-cm2 flask was added the entirety of the aforementioned first-generation virus fluid, followed by stationary cultivation at 28° C. for one hour. Subsequently, a serum-free SF-900 II medium (10 mL) was added to the culture, followed by stationary cultivation for four days. After completion of cultivation, cells were scraped out from the bottom of the flask by use of a cell scraper. The thus-collected cells were centrifuged at 3,000×g and 4° C. for 15 minutes, to thereby fractionate into the supernatant and the precipitate. The culture supernatant was collected and employed as a second-generation virus fluid.

5. Confirmation of Gene Insertion

Subsequently, insertion of a DNA into a cell was confirmed through the following procedure.

The precipitate obtained at the collection of the second-generation virus fluid was suspended in TE (200 μL), and a viral DNA was extracted in accordance with a manual of QIAamp DNA Mini Kit (QIAGEN). PCR was performed by use of the thus-extracted viral DNA as a template and the following primers.
SEQ ID NO: 14: PSC F2
SEQ ID NO: 15: PSC R2

To a 0.2-mL sample tube, the aforementioned viral DNA (1 µL), 2.5 mM dNTP (8 µL), KOD buffer (5 µL), 25 mM magnesium chloride solution (4 µL), primers PSC F2 and PSC R2 (4 pmol/mL each, 2.5 µL each), KOD DNA polymerase (product of TOYOBO) (1 µL), and sterilized pure water (26 µL) were added, and the mixture was sufficiently stirred. The mixture was subjected to PCR for 30 cycles, each cycle consisting of 94° C. for 30 seconds, 50° C. for 30 seconds, and 74° C. for 60 seconds.

The PCR product (5 µL) was subjected to electrophoresis on agarose gel, and the length of the amplified fragments was determined. A PCR product of a fragment having a target length was purified, and the sequences of the N-terminus side and the C-terminus side were determined, through use of the same reagents, apparatuses, and primers PSC F and PSC R as employed in the aforementioned "1. Construction of expression vector."

6. Production of Recombinant Virus Fluid

Insect cells (expresSF+, trade name, Protein Science) which were in the logarithmic growth phase during cultivation were diluted with a serum-free Sf-900 II medium so as to adjust the concentration to 1.5×106 cells/mL, and the diluted product (100 mL) was placed in a 250-mL Erlenmeyer flask. The aforementioned second-generation virus fluid (1 mL) was added thereto, and the mixture was subjected to shake cultivation at 130 rpm and 28° C. for three days. After completion of cultivation, the culture liquid was centrifuged at 3,000×g and 4° C. for 15 minutes, to thereby fractionate into the supernatant and the precipitate. The culture supernatant was collected and employed as a third-generation virus fluid.

7. Titer Determination

Sf9 cells (2.0×106) were plated onto a plate (diameter: 60 mm) and allowed to stand at 28° C. for one hour, whereby the cells were adhered to the bottom surface. Subsequently, the culture liquid was removed. Separately, the third-generation virus fluid was diluted with a serum-free Sf-900 II medium at dilution factors of 105, 106, 107, and 108. An aliquot (1 mL) of each of these solutions was added to the plate, followed by gentle shaking at room temperature for one hour. After removal of the plate supernatant (virus fluid), a serum-free Sf-900 II medium (4 mL) containing 0.5% SeaKemGTG agarose (product of BMA) was added to the plate, and stationary culture was performed at 28° C. for nine days. In each culture medium, the number of observed plaques was counted, thereby determining the titer.

8. Expression Test

Insect cells (expresSF+) were diluted with a serum-free Sf-900 II medium so as to adjust the concentration to 1.5×106 cells/mL, and the diluted product (100 mL/per flask) was placed in three 250-mL Erlenmeyer flasks. The aforementioned third-generation virus fluid was added thereto so as to attain MOIs of 0.5, 2, and 8, respectively. Each mixture was subjected to shake cultivation at 130 rpm and 28° C. for three days. After completion of cultivation, the culture liquid was centrifuged at 3,000×g and 4° C. for 15 minutes, to thereby fractionate into the supernatant and the precipitate.

9. Detection of Expression Product

Each of the samples collected in "8. Expression test" above was subjected to SDS-PAGE through a routine method. A protein was transferred to a blotting membrane through the semi-dry blotting method, and the expression product was detected by Western blotting under the below-mentioned conditions. Note that the DNA encoding factor G subunit α incorporated into the virus had been designed so as to express a His-tag-bound protein. Sample treatment: The supernatant was mixed with Laemmli Sample Buffer (product of BIO-RAD), and the mixture was heated at 99° C. for three minutes. The precipitate (200 µL) was mixed with PBS (200 µL), to thereby form a suspension. Laemmli Sample Buffer was added to the suspension, and the mixture was heated at 99° C. for three minutes.
Amount of applied sample: 20 µL/lane
SDS-PAGE gel: 12.5% gel (product of BIO-RAD)
Voltage application in SDS-PAGE: 150V, CV
Blotting membrane: PVDF
Voltage application in blotting: 15V, CV, 30 minutes
Antibody: PentaHis HRP Conjugate (product of QIAGEN)
Detection: ECL Detection Reagent (product of Amersham Biosciences)

10. Results

Analysis of the total nucleotide sequence after insertion to pPSC8 indicates that the obtained nucleotide sequence completely coincides with that of the DNA encoding factor G subunit α. Therefore, no mutation was found to be introduced through PCR. The nucleotide sequence analysis of the N-terminal portion and C-terminal portion of the target sequence in the recombinant virus has revealed that the nucleotide sequences of the two portions completely coincide with those of the DNA encoding factor G subunit α. Thus, the recombinant virus was found to have a nucleotide sequence of the DNA encoding factor G subunit α.

The titer was determined to be 3×108 pfu/mL.

In the results of "9. Detection of expressed product" above, a band attributed to reaction with an anti-His-Tag antibody was observed at a target position (about 75 kDa). Thus, expression of factor G subunit α was confirmed.

<2> Expression of Subunit β of Factor G

A cDNA encoding factor G subunit β was kindly offered by Dr. Tatsushi MUTA (Department of Molecular and Cellular Biochemistry, Graduate School of Medical Sciences, Kyushu University). The cDNA had been as prepared through a method disclosed in J. Biol. Chem., 269(2), p. 1370-1374 (1994). Factor G subunit β was expressed through the same procedure as employed in <1> above, and the expression product was analyzed. Details of these steps will next be described.

1. Construction of Expression Vector

A cDNA encoding factor G subunit β (Factor G-β/pFastbac1) was treated with BamHI/Hind III, and fragments (about 1,000 bp) having a target gene were collected. The sample was blunt-ended, and subsequently, ligated through mixing with Nru I-treated pPSC8. E. coli JM109 was transformed with the ligation product, to thereby form a transformant. A clone in which insertion of a target gene had been confirmed was inoculated to an LB medium (100 mL) containing 50 µg/mL ampicillin, and cultivated at 37° C. for one night. Proliferated cells were collected, and plasmids were purified in accordance with the manual of Plasmid Midi Kit (QIAGEN).

2. Co-transfection

To Sf9 cells (1.0×106) plated in a 25-cm2 flask was added a serum-free SF-900 II medium (200 µL) containing an expression vector harboring a cDNA encoding factor G subunit β (4.6 µg), a linear AcNPV DNA (85 ng), and LIPOFEC- TIN Reagent (5 μL). After the culture had been allowed to stand at 28° C. for six hours, a serum-free SF-900 II medium was further added so as to adjust the volume of the culture liquid to 5 mL. The culture was further cultivated at 28° C. for seven days, and the culture supernatant was collected, to thereby serve as a co-transfection solution.

3. Purification of Recombinant Virus

The recombinant virus was purified through the plaque assay method. The specific procedure is as follows.

Sf9 cells (2.0×106) were plated onto a plate (diameter: 60 mm) and allowed to stand at 28° C. for one hour, whereby the cells were adhered to the bottom surface. The aforementioned co-transfection solution was diluted with a serum-free Sf-900 II medium at dilution factors of 104, 105, 106, and 107. An aliquot (1 mL) of each of these solutions was added to the cells, followed by gentle shaking at room temperature for one hour. After removal of the plate supernatant (virus fluid), a serum-free Sf-900 II medium (4 mL) containing 0.5% SeaKemGTG agarose (product of BMA) was added to the plate, and stationary culture was performed at 28° C. for six days. From each culture medium, six plaques of infected insect cells including no polyhedra were collected. The plaques of each medium were suspended in a serum-free Sf-900 II medium (1 mL), to thereby serve as a virus fluid.

4. Amplification of Recombinant Virus

Next, amplification of the recombinant virus (preparation of recombinant virus fluid) was performed. The specific procedure was as follows.

To Sf9 cells (2.0×106) plated in a 25-cm2 flask was added each (0.5 mL) of the aforementioned virus fluids, followed by stationary cultivation at 28° C. for one hour. A serum-free SF-900 II medium was added to the culture so as to adjust the volume of the culture liquid to 5 mL, and the culture was further stationary-cultivated for three days, to thereby yield a first-generation virus fluid.

To Sf9 cells (6.0×106) plated in a 75-cm2 flask was added the entirety of the aforementioned first-generation virus fluid, followed by stationary cultivation at 28° C. for one hour. Subsequently, a serum-free SF-900 II medium (10 mL) was added to the culture, followed by stationary cultivation for four days. After completion of cultivation, cells were scraped out from the bottom of the flask by use of a cell scraper. The thus-collected cells were centrifuged at 3,000×g and 4° C. for 15 minutes, to thereby fractionate into the supernatant and the precipitate. The culture supernatant was collected and employed as a second-generation virus fluid.

5. Confirmation of Gene Insertion

Subsequently, insertion of a DNA into a cell was confirmed through the following procedure.

The precipitate obtained at the collection of the second-generation virus fluid was suspended in TE (200 μL), and a viral DNA was extracted in accordance with a manual of QIAamp DNA Mini Kit (QIAGEN). PCR was performed by use of the thus-extracted viral DNA as a template and the following primers.

SEQ ID NO: 16: PSC F2
SEQ ID NO: 17: PSC R2

To a 0.2-mL sample tube, the aforementioned viral DNA (1 μL), 2.5 mM dNTP (8 μL), KOD buffer (5 μL), 25 mM magnesium chloride solution (4 μL), primers PSC F2 and PSC R2 (4 pmol/mL each, 2.5 μL each), KOD DNA polymerase (product of TOYOBO) (1 μL), and sterilized pure water (26 μL) were added, and the mixture was sufficiently stirred. The mixture was subjected to PCR for 30 cycles, each cycle consisting of 94° C. for 30 seconds, 50° C. for 30 seconds, and 74° C. for 60 seconds.

The PCR product (5 μL) was subjected to electrophoresis on agarose gel, and the length of amplified fragments was determined. A PCR product of a fragment having a target length was purified, and the sequences of the N-terminus side and the C-terminus side were determined, through use of the same reagents and apparatuses as employed in the aforementioned "<1>-1. Construction of expression vector." The following primers were employed.

SEQ ID NO: 18: PSC F
SEQ ID NO: 19: PSC R

6. Production of Recombinant Virus Fluid

Insect cells (expresSF+, trade name, Protein Science) which were in the logarithmic growth phase during cultivation were diluted with a serum-free Sf-900 II medium so as to adjust the concentration to 1.5×106 cells/mL, and the diluted product (100 mL) was placed in a 250-mL Erlenmeyer flask. The aforementioned second-generation virus fluid (1 mL) was added thereto, and the mixture was subjected to shake cultivation at 130 rpm and 28° C. for three days. After completion of cultivation, the culture liquid was centrifuged at 3,000×g and 4° C. for 15 minutes, to thereby fractionate into the supernatant and the precipitate. The culture supernatant was collected and employed as a third-generation virus fluid.

7. Titer Determination

Sf9 cells (2.0×106) were plated onto a plate (diameter: 60 mm) and allowed to stand at 28° C. for one hour, whereby the cells were adhered to the bottom surface. Subsequently, the culture liquid was removed. Separately, the third-generation virus fluid was diluted with a serum-free Sf-900 II medium at dilution factors of 105, 106, 107, and 108. An aliquot (1 mL) of each of these solutions was added to the plate, followed by gentle shaking at room temperature for one hour. After removal of the plate supernatant (virus fluid), a serum-free Sf-900 II medium (4 mL) containing 0.5% SeaKemGTG agarose (product of BMA) was added to the plate, and stationary culture was performed at 28° C. for nine days. In each culture medium, the number of observed plaques was counted, thereby determining the titer.

8. Expression Test

Insect cells (expresSF+) were diluted with a serum-free Sf-900 II medium so as to adjust the concentration to 1.5×106 cells/mL, and the diluted product (100 mL/per flask) was placed in three 250-mL Erlenmeyer flasks. The aforementioned third-generation virus fluid was added thereto so as to attain MOIs of 0.5, 2, and 8, respectively. Each mixture was subjected to shake cultivation at 130 rpm and 28° C. for three days. After completion of cultivation, the culture liquid was centrifuged at 3,000×g and 4° C. for 15 minutes, to thereby fractionate into the supernatant and the precipitate.

9. Detection of Expression Product

Each of the samples collected in "8. Expression test" above was subjected to SDS-PAGE and Western blotting through the same method as employed in "<1>-9. Detection of expression product. Note that the DNA encoding factor G subunit β incorporated into the virus had been designed so as to express a His-tag-bound protein.

10. Results

The nucleotide sequence analysis of the N-terminal portion and C-terminal portion of the target sequence in the recombinant virus has revealed that the nucleotide sequences of the two portions completely coincide with those of the DNA encoding factor G subunit β. Thus, the recombinant virus was found to have a nucleotide sequence of the DNA encoding factor G subunit β.

The titer was determined to be 1.7×108 pfu/mL.

In the results of "9. Detection of expressed product" above, a band attributed to reaction with an anti-His-Tag antibody was observed at a target position (about 37 kDa). Thus, expression of factor G subunit β was confirmed.

<3> Co-expression of Subunits α and β of Factor G

The third-generation virus fluids prepared in <1> and <2> above for producing factor G subunits α and β, respectively, were employed so as to co-express both subunits.

Insect cells (expresSF+) were diluted with a serum-free Sf-900 II medium so as to adjust the concentration to 1.5×106 cells/mL, and the diluted product (50 mL/per flask) was placed in three 125-mL Erlenmeyer flasks. The aforementioned third-generation virus fluids, which had been prepared for producing factor G subunits α and β, were added thereto at the following proportions. Each mixture was subjected to shake cultivation at 130 rpm and 28° C. for three days. After completion of cultivation, the culture liquid was centrifuged at 3,000×g and 4° C. for 15 minutes, to thereby fractionate into the supernatant and the precipitate. The supernatant was frozen for preservation.

Sample 1:
　subunit α:subunit β=1:0 (by MOI)
　subunit α:subunit β=57.7:0 (by virus amount (μL))

Sample 2:
　subunit α:subunit β=0:1 (by MOI)
　subunit α:subunit β=0:187.5 (by virus amount (μL))

Sample 3:
　subunit α:subunit β=1:1 (by MOI)
　subunit α:subunit β=57.7:187.5 (by virus amount (μL))

Sample 4:
　subunit α:subunit β=1:2 (by MOI)
　subunit α:subunit β=57.7:375 (by virus amount (μL))

Sample 5:
　subunit α:subunit β=1:4 (by MOI)
　subunit α:subunit β=57.7:750 (by virus amount (μL))

Sample 6:
　subunit α:subunit β=2:1 (by MOI)
　subunit α:subunit β=115.4:187.5 (by virus amount (μL))

Sample 7:
　subunit α:subunit β=4:1 (by MOI)
　subunit α:subunit β=230.8:187.5 (by virus amount (μL))

The procedure as employed in <1>-9 above was repeated, except that 10% gel (product of BIO-RAD) was employed as the SDS-PAGE gel and an anti-GST-HRP Conjugate (product of Amersham Biosciences) was employed as an antibody for detection, to thereby perform SDS-PAGE and Western blotting of the supernatants. Note that the DNA encoding factor G subunit α and that encoding factor G subunit β incorporated into the virus had been designed so as to express GST-bound proteins.

As a result, bands attributed to reaction with an anti-GST antibody were observed at target positions (about 75 kDa and 37 kDa). Thus, expression of factor G subunits α and β was confirmed.

Separately, the supernatant was purified by using Ni Sepharose 6 Fast Flow (product of Amersham Biosciences). After desalting and concentration of the eluate, the procedure as employed in <1>-9 above was repeated, except that 5-20% gradient gel (product of ATTO) was employed as the SDS-PAGE gel, mixture of an anti-Factor G subunit α serum and an anti-Factor G subunit β serum (kindly offered by Dr. Tatsushi MUTA (Department of Molecular and Cellular Biochemistry, Graduate School of Medical Sciences, Kyushu University)) was employed as a first antibody, HRP-conjugated anti-rabbit IgG antibody was employed as a second antibody and Konica Immunostain HRP-100 (product of Konica Minolta) was employed as a reagent for detection, to thereby perform SDS-PAGE and Western blotting of the eluate. Note that the DNA encoding factor G subunit α and that encoding factor G subunit β incorporated into the virus had been designed so as to express His-tag-bound proteins.

As a result, bands attributed to reaction with the mixture of an anti-Factor G subunit α serum and an anti-Factor G subunit β serum were observed at target positions (about 75 kDa and 37 kDa). Thus, expression of factor G subunits α and β was confirmed.

After cultivation, the supernatant was collected from each of the aforementioned seven samples, and whether or not the expressed protein maintains factor G activity was checked.

Specifically, the supernatant fraction after completion of cultivation was diluted at a factor of 11 times with an ice-cooled 50 mM Tris-HCl buffer (pH: 7.5) containing 150 mM NaCl. To the diluted product (25 μL), there were added a pro-clotting enzyme derived from a lysate (25 μL), dextran (final concentration: 2.4%), Tris-HCl buffer (pH: 8.0) (final concentration: 0.08 M), MgSO4 (final concentration: 0.08 M), CaCl2 (final concentration: 0.16 mM), distilled water for injection (10 μL), Boc-Leu-Gly-Arg-pNA substrate (see Japanese Patent Application laid-Open (kokai) No. 08-122334) (final concentration: 0.53 mM), and BG (0.25 ng), followed by adjusting the total volume to 125.1 μL. The mixture was allowed to react at 37° C. for 24 hours. After completion of reaction, absorbance of the sample was measured at 405 nm (blank) and 492 nm. Factor G derived from a lysate was employed as a positive control. The experiment was performed twice, and absorbance measures were averaged. The results are as follows.

Results:
　Sample 1 (α:β3=1:0): 0.166
　Sample 2 (α:β3=0:1): 0.167
　Sample 3 (α:β=1:1): 0.278
　Sample 4 (α:β3=1:2): 0.190
　Sample 5 (α:β3=1:4): 0.169
　Sample 6 (α:β3=2:1): 0.730
　Sample 7 (α:β3=4:1): 1.078
　factor G: 1.328

As is clear from the results, Samples 6 and 7, which had been prepared with controlling a MOI of virus harboring a DNA encoding subunit α to be higher than a MOI of virus harboring a DNA encoding subunit β during infection of cells with the virus, were found to have factor G activity. The analysis also indicated that intrinsic functions of the thus-expressed subunits α and β were not impaired.

The thus-produced factor G can be reacted with BG. Therefore, as-produced factor G may be employed for assaying BG or diagnosing mycosis.

As described hereinabove, the present invention provides a tool and a method for mass-expressing factor G derived from a horseshoe crab or a subunit forming the factor. Factor G and subunit(s) forming the factor produced according to the present invention may be employed as assay/diagnosis tools for BG assay, mycosis diagnosis, and other purposes, as well as laboratory reagents.

What is claimed is:

1. An insect-derived cell comprising:
   a first baculovirus harboring a DNA encoding wild-type subunit α of factor G derived from *Tachypleus tridentatus*;
   a second baculovirus harboring a DNA encoding wild-type subunit β of factor G derived from *Tachypleus tridentatus*; and,
   wherein the cell has been co-transfected by the first baculovirus and the second baculovirus; and,
   wherein a multiplicity of infection with the first baculovirus is higher than that with the second baculovirus.

2. The cell according to claim 1, wherein the DNA encoding wild-type subunit a of factor G is a DNA encoding a polypeptide defined by SEQ ID No: 2 and the DNA encoding wild-type subunit β of factor G is a DNA encoding a polypeptide defined by SEQ ID No: 4.

3. The cell according to claim 1, wherein the DNA encoding wild-type subunit a of factor G is a DNA having a nucleotide sequence defined by nucleotides 1 to 2022 in SEQ ID NO: 1 and the DNA encoding wild-type subunit β of factor G is a DNA having a nucleotide sequence defined by nucleotides 1 to 930 in SEQ ID NO: 3.

4. The cell according to claim 1, wherein the first baculovirus is nuclear polyhedrosis virus.

5. The cell according to claim 1, wherein the second baculovirus is nuclear polyhedrosis virus.

6. The cell according to claim 1, wherein the first baculovirus and the second baculovirus are nuclear polyhedrosis viruses.

7. The cell according to claim 1, wherein a ratio of the multiplicity of infection of the former baculovirus to the latter baculovirus is from 1.5:1 to 64:1.

* * * * *

UNITED STATES PATENT AND TRADEMARK OFFICE
CERTIFICATE OF CORRECTION

| | |
|---|---|
| PATENT NO. | : 7,867,733 B2 |
| APPLICATION NO. | : 12/430681 |
| DATED | : January 11, 2011 |
| INVENTOR(S) | : Tamura |

It is certified that error appears in the above-identified patent and that said Letters Patent is hereby corrected as shown below:

Claim 2, Column 35, Line 14    Replace "a" with "α" -- ing wild-type subunit [[a]] α of factor G is a DNA encoding a --

Claim 3, Column 36, Line 2    Replace "a" with "α" -- ing wild-type subunit [[a]] α of factor G is a DNA having a nucle --

Signed and Sealed this
Fifth Day of April, 2011

David J. Kappos
*Director of the United States Patent and Trademark Office*